United States Patent [19]
Koskinen et al.

[11] Patent Number: 5,646,729
[45] Date of Patent: Jul. 8, 1997

[54] SINGLE-CHANNEL GAS CONCENTRATION MEASUREMENT METHOD AND APPARATUS USING A SHORT-RESONATOR FABRY-PEROT INTERFEROMETER

[75] Inventors: Yrjö Koskinen; Ari Lehto, both of Helsinki, Finland; Simo Tammela, Espoo; Martti Blomberg, Vantaa; Markku Orpana, Espoo; Altti Torkkeli, Espoo, all of Finland

[73] Assignee: Vaisala Oy, Helsinki, Finland

[21] Appl. No.: 573,759

[22] Filed: Dec. 18, 1995

Related U.S. Application Data

[63] Continuation of Ser. No. 177,404, Jan. 5, 1994, abandoned.

[30] Foreign Application Priority Data

Jan. 13, 1993 [FI] Finland ............... 930127

[51] Int. Cl.[6] ............... G01B 9/02; G02B 27/00
[52] U.S. Cl. ............... 356/352; 359/260; 359/578
[58] Field of Search ............... 356/352; 359/260, 359/578, 579

[56] References Cited

U.S. PATENT DOCUMENTS

| | | | |
|---|---|---|---|
| 4,547,801 | 10/1985 | Haisma et al. | 356/352 |
| 4,790,635 | 12/1988 | Apsley | 359/260 |
| 5,040,895 | 8/1991 | Laurent et al. | 356/352 |
| 5,073,004 | 12/1991 | Clayton et al. | 356/352 |
| 5,111,329 | 5/1992 | Gajewski et al. | 359/260 |
| 5,142,414 | 8/1992 | Koehler | 356/352 |
| 5,218,422 | 6/1993 | Zoechbauer | 356/352 |
| 5,225,888 | 7/1993 | Selwyn et al. | 356/352 |
| 5,321,539 | 6/1994 | Hirabayashi et al. | 356/352 |

OTHER PUBLICATIONS

Aratani, K. et al, "Process For Surface Micromachined Beams For a Tuneable Interferometer Array In Silicon," pp. 346, Oct. 1992.

Parameswaran, M. et al, *IEEE Electron Device Letters,* vol. 12, No. 2, Feb. 1991, "Micromachined Thermal Radiation Emitter from a Commercial CMOS Process", pp. 57–59.

Mastrangelo, Carols H. et al, *IEEE Transactions On Electron Devices,* vol. 39, No. 6, Jun. 1992, "Electrical and Optical Characteristics of Vacuum Sealed Polysilicon Microtaps", pp. 1363–1375.

*Primary Examiner*—Frank Gonzalez
*Assistant Examiner*—Jason D. Eisenberg
*Attorney, Agent, or Firm*—Birch, Stewart, Kolasch & Birch, LLP

[57] ABSTRACT

A single-channel gas concentration measurement method and apparatus. According to the method, a radiant source is employed to generate a measuring signal, the measuring signal is subsequently directed to a measurement object containing a gas mixture to be measured, the measuring signal is subsequently bandpass filtered using at least two passband wavelengths, and the filtered measuring signals are detected by a detector. According to the invention, the bandpass filtering step is implemented by a single electrostatically tunable, short-resonator Fabry-Perot interferometer.

14 Claims, 5 Drawing Sheets

FIG. 3
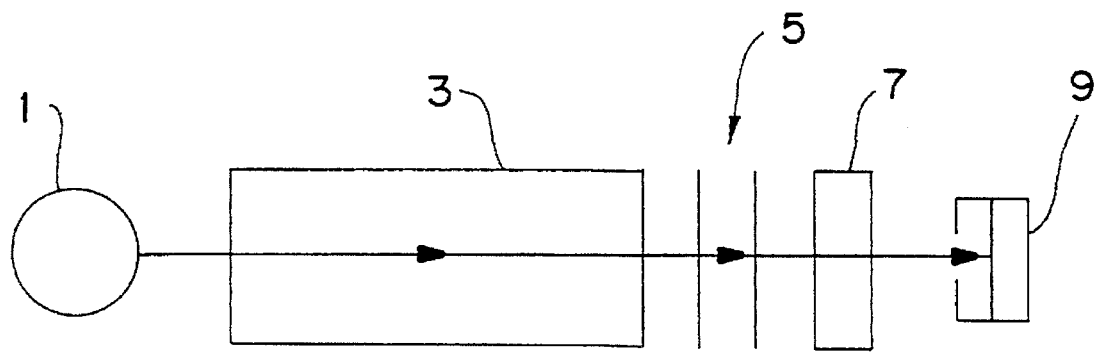
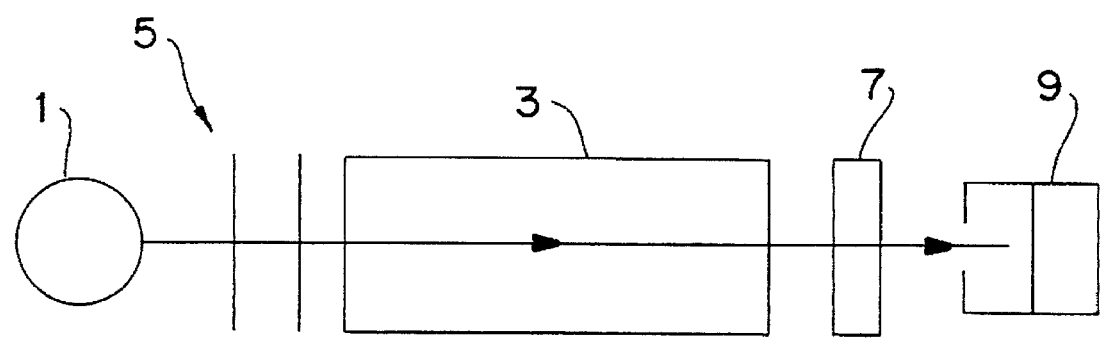
FIG. 4

SINGLE-CHANNEL GAS CONCENTRATION MEASUREMENT METHOD AND APPARATUS USING A SHORT-RESONATOR FABRY-PEROT INTERFEROMETER

This application is a continuation, of application Ser. No. 08/177,404 filed on Jan. 5, 1994, now abandoned.

The present invention relates to a single-channel method and apparatus for gas concentration measurement.

The invention also concerns a single-channel gas concentration measurement apparatus.

DESCRIPTION OF THE RELATED ART

Gas concentration is conventionally measured by means of measurement apparatuses based on nondispersive IR techniques (NDIR). Such measurement systems comprised of discrete components typically include the following parts: a radiant source, a measurement channel, a detector and a filter for selecting a desired wavelength band for the measurement. The filter employed typically is an interference filter. The filter is used for selecting the wavelength band that is allowed to pass from the radiant source via the measurement channel to the detector. Due to the aging and instability of the radiant source, some embodiments have additionally employed a mechanically changeable pair of filters adapted in front of the detector. The filter pair is comprised of two optical bandpass filters of which one filter is tuned to pass a desired spectral line of the gas being measured, while the other filter is tuned to reference wavelength at which the gas being measured has no spectral absorption line. The bandpass filters are changed during the measurement by means of, e.g., mounting them on a rotating disc.

The disadvantages of the above-described technique include the relatively high price of the bandpass filter and the mechanical changer implementation of the bandpass filter set which necessitates maintenance at short intervals. A mechanical implementation is very difficult to miniaturize suitable for contemporary compact measurement apparatuses.

Also the harsh environmental conditions imposed on the measurement apparatuses frequently set such strict requirements as to make a reliable mechanical implementation of the bandpass filter changer economically impossible. The physically separated surfaces of the different filters involved in the measurement become contaminated at different rates thus causing uncontrollable measurement errors.

To measure gas concentrations, the measurements have utilized long, adjustable Fabry-Perot interferometers exhibiting "comb-like" bandpass characteristics due to the relatively large length of the interferometric resonators.

Large-scale industrial fabrication of long interferometers is incompatible with the current surface micromachining techniques. A "comb-like" bandpass characteristic is tunable only for a single spectrum, whereby gas analysis, for instance, can be carried out on the concentration of a single gas (=molecule species) alone.

SUMMARY OF THE INVENTION

It is an object of the present invention to overcome the disadvantages related to the above-described prior-art techniques and to achieve an entirely novel single-channel gas concentration measurement method and apparatus.

The invention is based on using an electrostatically controlled, short Fabry-Perot interferometer as the alternating bandpass filter element in the measurement apparatus.

More specifically, the method according to the invention is characterized by the bandpass filtering step being implemented by means of a single electrically tunable, short-resonator Fabry-Perot interferometer.

Furthermore, the apparatus according to the invention is characterized by the bandpass filtering step being implemented by means of a single electrically tunable, short-resonator Fabry-Perot interferometer.

The invention offers significant benefits. As the measurement is optically performed in a dual-channel fashion, a reference signal is obtained suitable for compensation of ageing phenomena in the radiant source. However, the physical implementation of the method is in a single-channel fashion, since the radiation measured travels along the same path at all times. Therefore, the contamination of the optical surfaces has the same effect both during the actual measurement period and the reference measurement period, because the only modulated property in the measurement is the length of the interferometer resonator. The effect of contamination is thus automatically taken into account by virtue of the reference measurement.

Further, the life of the interferometer construction is practically unlimited, because its length is modulated only by a small amount and such change of length is kept entirely within the elastic range of the substrate material used.

The absorptive filter element of prior-art constructions is a discrete component which is mechanically mounted to a predetermined point on the optical path. By contrast, in an embodiment according to the invention, the filter is fabricated in a single manufacturing process directly onto the surface of the interferometer. Such an implementation is more compact and cheaper in production.

The aperture of the interferometer in prior-art constructions is a discrete component which is mechanically mounted to a predetermined point on the optical path. Contrastingly, in an embodiment according to the invention, the aperture is fabricated in a single manufacturing process directly onto the surface of the interferometer. Such an implementation is more compact and cheaper to produce. The alignment of a discrete aperture element may be awkward. By contrast, in the implementation according to the invention, the aperture is automatically aligned.

The manufacturing method according to the invention makes it possible to fabricate interferometers with an area greater than one square millimeter for the VIS-IR (visible infrared) range, so their use is not limited to optical fiber systems.

In the construction according to the invention, separate deflection electrodes need not be provided to assure the parallelity of the interferometer mirrors during their movement, since the mirrors are supported by the entire length of their edges, and owing to the planar process employed, the height of the interferometer cavity is the same at all places.

The temperature sensitivity of interferometer element according to the invention is extremely low, because the length of the interferometer cavity is practically constant with respect to varying temperature.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention is next examined in greater detail with the help of exemplifying embodiments illustrated in the appended drawings, in which:

FIG. 3 shows diagrammatically an embodiment of the measurement apparatus according to the invention;

FIG. 4 shows diagrammatically an alternative embodiment of the measurement apparatus according to the invention;

DETAILED DESCRIPTION OF THE PREFERRED EMBODIMENTS

The intensity I of radiation incident on the detector is dependent on the absorption in the measurement channel according to the Lambert-Beer's law $$I = I_o e^{-kcx} \quad (1)$$

where $I_o$ the intensity of radiation incident on the detector, k is the extinction coefficient and c is the concentration of the gas being measured and x is the length of the measurement channel. The extinction coefficient k is strongly dependent on the measurement wavelength. The Fabry-Perot interferometer employed in the invention has a construction which facilitates electrostatic control of the resonator length. Simultaneously, also the transmitted passband wavelengths are modulated. The basic equation for the Fabry-Perot interferometer is $$2d = n\lambda \quad (2)$$

where d is the distance between the resonator mirrors, n is an integer (=axial mode number of interferometer resonator, or order number of interference) and $\lambda$ is the wavelength. The refractive index of the medium between the mirrors is assumed to be 1. In interferometers of conventional design the value of n typically is in the order of 100 to 100,000. This invention employs a short-resonator interferometer in which n is 1 to 3. The passband width B (=FWHM) of the interferometer is a function of the reflectance r of the mirrors and the distance d between the mirrors:

$$B = \frac{1-r}{\sqrt{r}} \frac{\lambda^2}{2\pi d} \quad (3)$$

The free spectral range FSR between the spectral lines corresponding to different values of interferometer order number means the spacing between the adjacent transmitted wavelengths. The FSR can be computed from Eq. (2) for values n and n+1 of the order number n:

$$\lambda_n - \lambda_{n+1} = \frac{2d}{n} - \frac{2d}{n+1} = \frac{2d}{n(n+1)} \quad (4)$$

Figure 1:
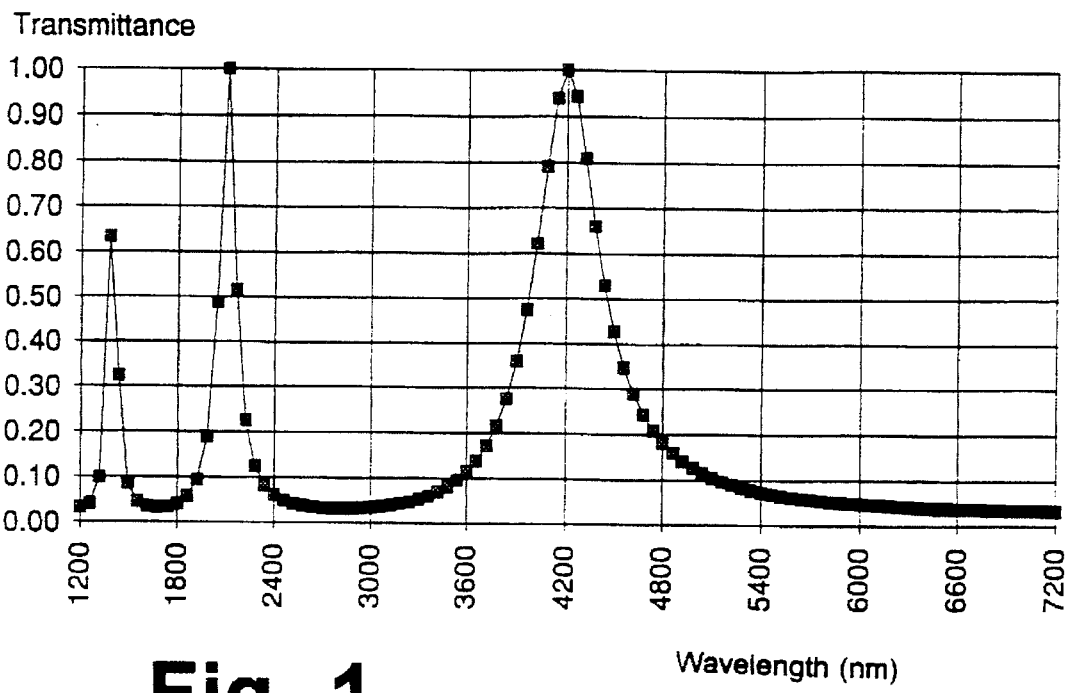
FIG. 1 shows graphically the bandpass properties of a short Fabry-Perot interferometer according to the invention.

As is evident from Eq. (4), the FSR increases when n is decreased. A large value of FSR makes the cancellation of spectral lines of adjacent interferometer order numbers easy by means of, e.g., a cut-off filter. In an interferometer fabricated by virtue of surface micromachining techniques, the distance d can be 2.1 µm and n=1. The value of FSR will then be 2.1 µm. The computed transmittance of the interferometer for r=0.7 is shown in FIG. 1.

Figure 2:
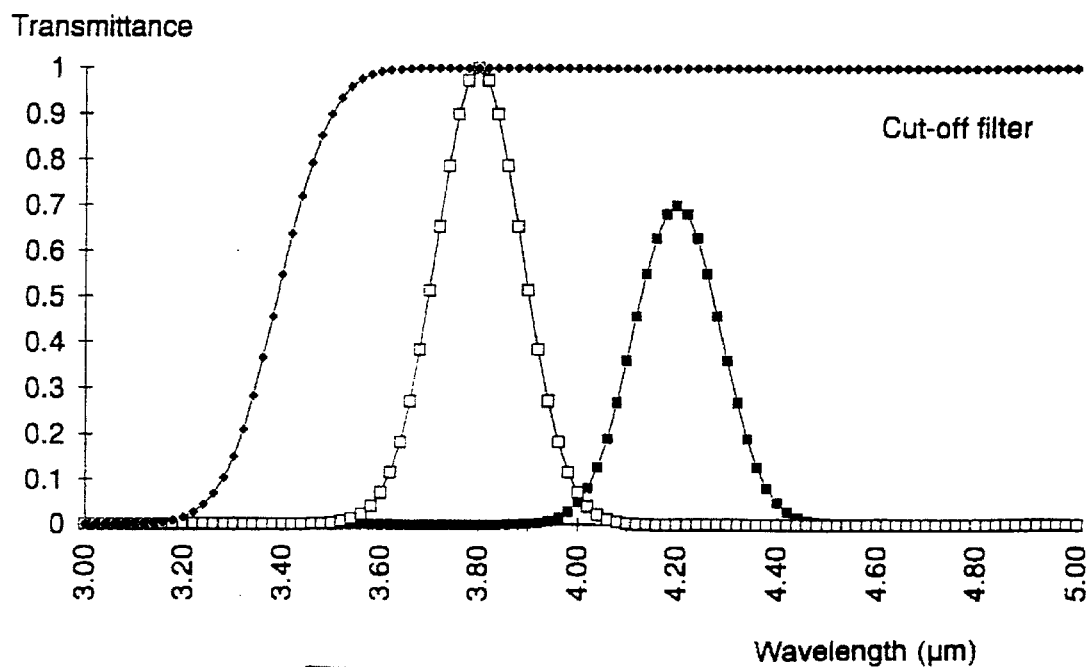
FIG. 2 shows graphically the measurement and calibration wavelength bands according to the invention.

With reference to FIG. 2, the transmittance of the Fabry-Perot interferometer complemented with a cut-off filter is shown for two different lengths of the interferometer. In this exemplifying graph the intensity admitted from the measurement channel at 4.2 µm wavelength is reduced by absorption from value 1 to value 0.7. The width of the transmitted wavelength band is selected so that the "comb-like" absorption spectrum of carbon dioxide at 4.2 µm wavelength fits within said wavelength band. When the length of the interferometer is shortened appropriately, it transmits at 3.8 µm wavelength at which no absorption occurs in the measurement channel, that is, at which wavelength the extinction coefficient k low. Accordingly, the intensity incident on the detector is proportional to the output intensity of the radiant source, and this intensity value can be used as a reference for the measurement signal from the measurement channel. The cut-off filter is employed to prevent wavelengths shorter than approx. 3.2 µm from reaching to the detector.

The measurement takes place so that the interferometer length is modulated so as to make it transmit at the 3.8 µm wavelength when the reference measurement is to be performed in this exemplifying embodiment. Then, the actual measurement is performed at the 4.2 µm wavelength. An alternative arrangement is such in which the unmodulated length of the interferometer is selected to transmit at a reference wavelength of 4.4 µm, for instance, while for the actual measurement, the interferometer resonator length is shortened by an applied electric field to transmit at 4.2 µm during the actual measurement.

The effects of slow drift in the radiant source output and of stray radiation can be reduced by modulating the radiant source, whereby an AC output signal is obtained from the detector.

With reference to FIG. 3, the function of the apparatus according to the invention is described. The method employed is such a modification of single-channel NDIR measurement in which the filters are changed electrically rather than mechanically. A radiant source 1 emits wide-spectrum radiation which propagates through a measurement channel 3 into a Fabry-Perot interferometer 5 performing as a filter. The wavelengths transmitted through the (multiple) passband(s) of this filter element are taken to a cut-off filter 7, which transmits wavelengths only longer than a certain cut-off wavelength. The intensity of the transmitted wavelength lines is measured by means of a detector 9.

Advantageously, the radiant source of the measurement apparatus is a wide-spectrum radiant source 1. This element can be, e.g., a wideband LED, a miniature incandescent lamp, a so-called microlamp made from polycrystalline silicon, or any other such a wideband radiant source that can be electrically modulated up to a frequency of approx. 1 kHz. The length of the measurement channel 3 can be varied in a wide range and its design is dependent on the concentration and absorption characteristics of the measured gas.

The Fabry-Perot interferometer 5 can be implemented by means of surface micromachining[3], whereby its fabrication can be suited to large-scale production techniques at a low price in mass quantities. Using the surface micromachining techniques, layers of a few micrometers maximum are deposited stepwise onto a substrate, after which the layers are then patterned, etched and doped as required in the method.

Any cut-off filter type of conventional optics can be employed as the cut-off filter 7. The detector 9 can be a pyroelectric, thermopile or photodiode detector depending on the wavelength range and intensity employed. The cut-off filter 7 can also perform as the radiation entrance window of the detector enclosure.

Alternatively, a construction shown in FIG. 4 can be used in which the Fabry-Perot interferometer 5 is adapted in conjunction with the radiant source 1. Then, the radiant source 1 performs as a narrow-spectrum source. Analogously, the cut-off filter 7 can be mounted in conjunction with that end of the measurement channel 3 which faces the radiant source 1.

Figure 5:
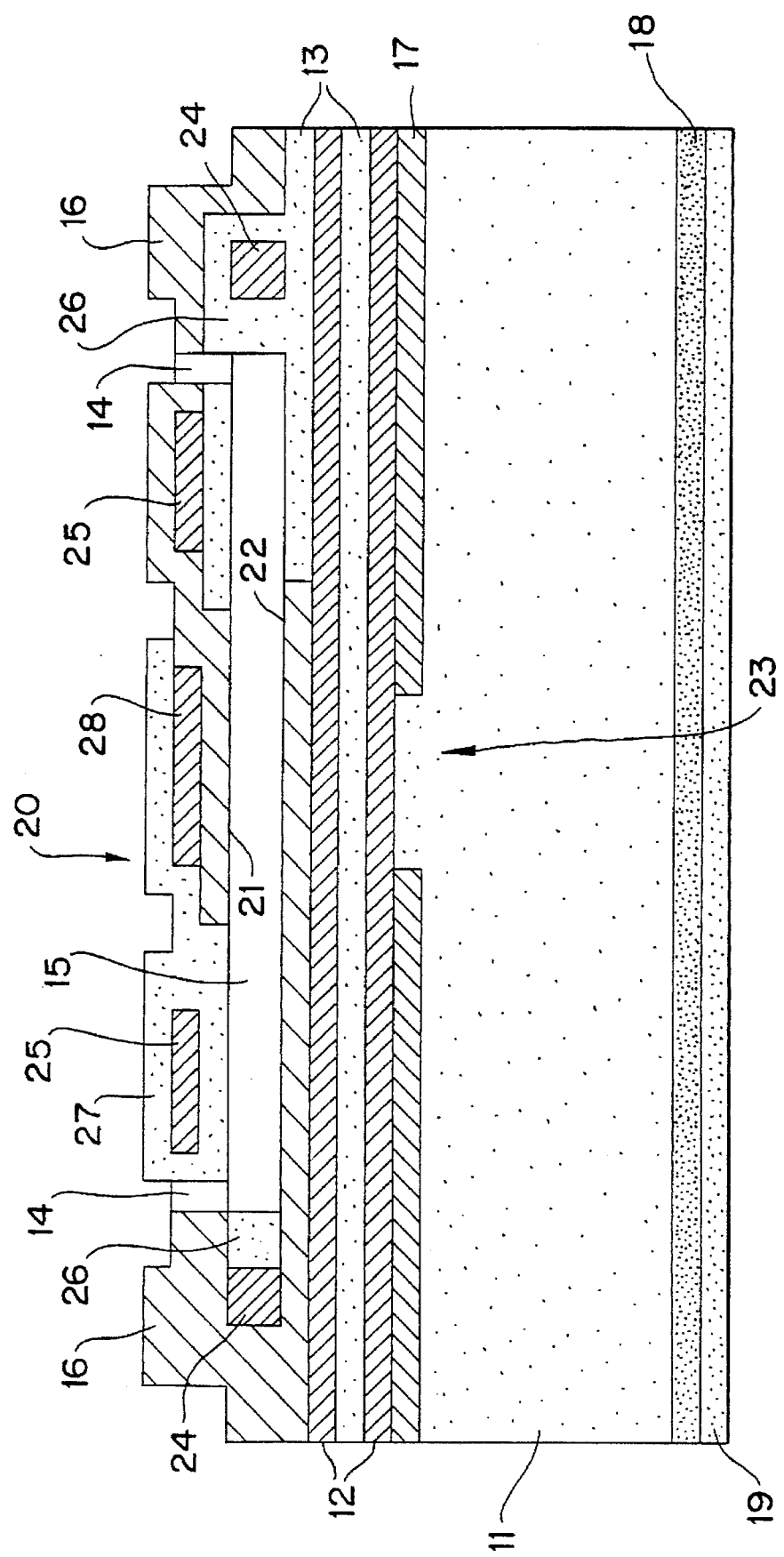
FIG. 5 shows a side view of a interferometer structure according to the invention.
Figure 6:
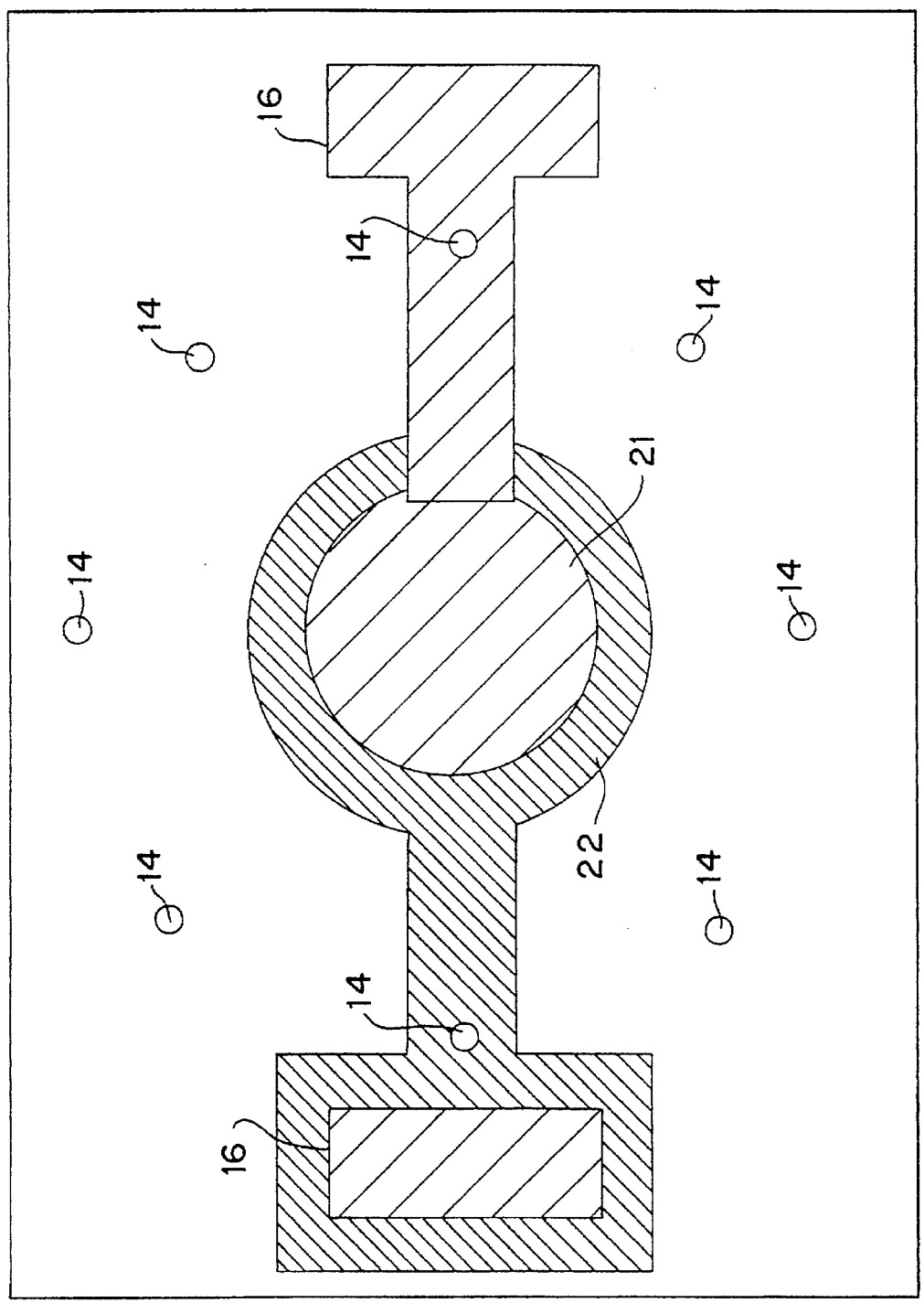
FIG. 6 shows the top view of the interferometer structure illustrated in FIG. 5.

With reference to FIG. 5, the cross section of the interferometer according to the invention is shown. The lower mirror of the interferometer is formed by alternating silicon dioxide layers 12 and polycrystalline silicon layers 13 which are deposited onto a substrate 11. The wavelength of the passband is determined by the height of an air gap 15, which is etched with, e.g., hydrofluoric acid (HF) via holes 14 to the interior of the multilayer structure. Initially, the space 15 is filled by solid oxide. The size of the holes 14 is in the order a few micrometers, and they are circularly aligned as shown in FIG. 6. The area 20 is the optically active area of the interferometer upper mirror, that is, the area which moves in a planar manner during the modulation of the interferometer. The upper mirror is deposited as alternating silicon 21, 27 and oxide layers 28. The darkened areas of the silicon layers 21, 27 indicate where the silicon is doped electrically conducting.

The modulating voltage is applied between metal contacts 16. A polycrystalline silicon layer 26 annularly enclosed by a silicon dioxide layer 24 acts as a barrier to the etchant during the etching-away of the layer 15. Layers 25 are silicon dioxide layers of the upper mirror membrane structure. A hole 23 in a metallic layer 17 acts as an aperture 23 of the interferometer, thus preventing transmission of radiation outside the optically active central area. The cut-off filter element is formed by a layer 18. This element is comprised of one or greater number of $\lambda/2$ layers of such a material that has desired absorption characteristics. The essential for the function of the invention is herein that the layer 18 is particularly a $\lambda/2$ layer (or a multiple thereof), because such a layer causes no transmission losses caused by refractive index discontinuities between the layers adjacent to such a layer. In fact such a layer 18 can be deposited anywhere between any two dielectric layers. An antireflection coating is provided by layer 19 which can be, e.g., a $\lambda/4$ layer of silicon nitride. The scaling of the elements in the diagram are not entirely true to reality as the area 28, for instance, in practice covers approximately half of the crosswise dimension of the resonator cavity 15. Correspondingly, the areas 25 which in practice form a contiguous ring are wider that depicted herein, whereby also the polycrystalline silicon layer remains cross-wise narrower than that illustrated in the diagram. The metallic layer aperture 23 can alternatively be formed by doping an area of equivalent pattern into the silicon substrate 11 as heavily doped silicon is opaque to radiation. When patterned by doping, the aperture 23 can also be located in the underlying layer 13 or on the lower surface of the substrate 11. Preferably, the sheet resistivity ($\Omega/\square$) of the doped area is less than 5 ohms. Suitable dopants are boron and phosphorus, for instance.

With reference to FIG. 6, the interferometer is shown in a top view.

Figure 7:
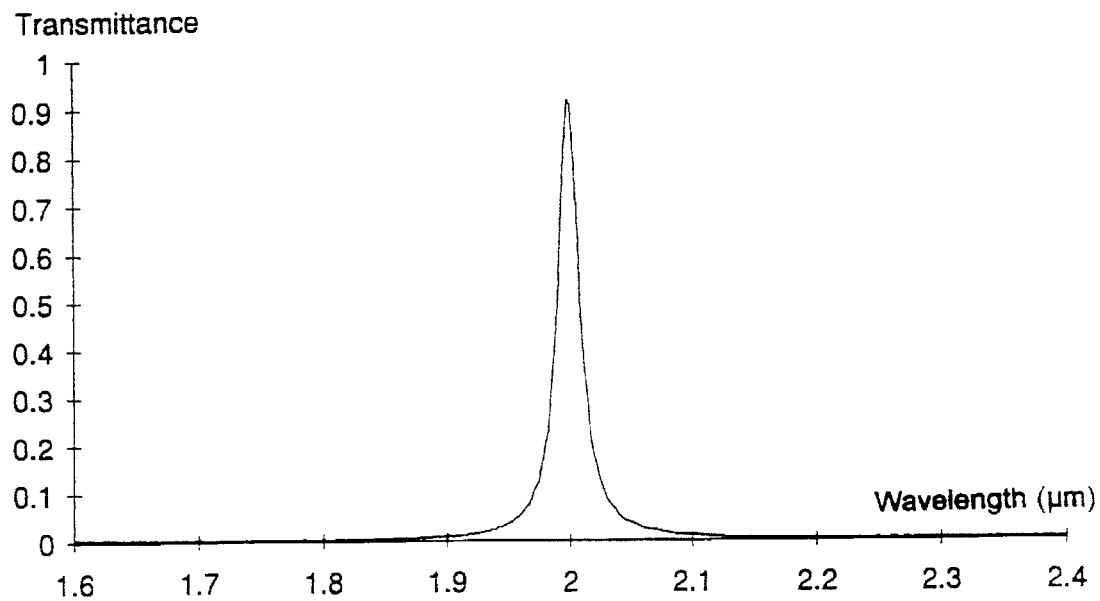
FIG. 7 shows graphically the transmittance characteristics of the interferometer illustrated in FIG. 5.

With reference to FIG. 7, the computed transmittance characteristics of the interferometer illustrated in FIG. 5 is shown in an exemplifying manner plotted about a center wavelength of two micrometers. The existence of the layer 18 has no effect on the shape of the passband curve.

Figure 8:
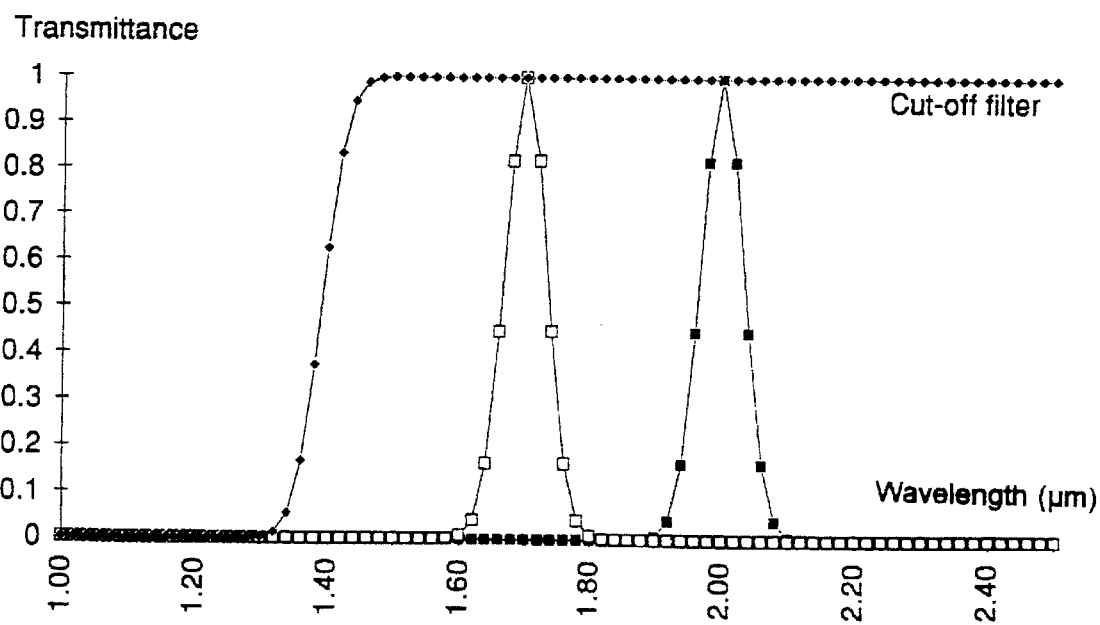
FIG. 8 shows graphically the computed transmittance characteristics of the interferometer illustrated in FIG. 5 for two different lengths of the interferometer.

With reference to FIG. 8, the cut-off filtered passband of the Fabry-Perot interferometer illustrated in FIGS. 5 and 6 is plotted for two different lengths of the interferometer resonator. In a state of no modulation voltage, the interferometer passband is centered at 2 μm, while with the modulation, the passband is at 1.4 μm. The cut-off filter prevents radiation at wavelengths shorter than approx. 1.3 μm from reaching the detector.

As the details of the manufacturing process used for fabricating the interferometer are dependent on the available equipment, the manufacturing process described below must be understood as an exemplifying procedure. A person skilled in the art should be familiar with the methods employed in the fabrication of the structure illustrated in FIG. 5. The manufacturing process includes no details different from the standard processes of surface micromachining techniques.

The silicon dioxide layers can alternatively be replaced by silicon nitride layers.

Top side:
1. The substrate wafer used is a silicon wafer 11 oriented in the (100) direction and polished on both sides.
2. The wafer 11 is washed.
3. A metallic layer 17 is deposited to a thickness of approx. 50 nm. The alloy in the metallic layer 17 can be, e.g., TiW (titanium tungsten).
4. Aperture holes 23 are patterned.
5. A first $\lambda/4$ silicon dioxide layer 12 is grown.
6. A first $\lambda/4$ polycrystalline silicon layer 13 is grown.
7. A second $\lambda/4$ silicon dioxide layer 12 is grown.
8. A second $\lambda/4$ polycrystalline silicon layer 13 is grown.
9. The latter layer is doped electrically conducting for the parts darkened in the diagram.
10. A $\lambda/2$ silicon dioxide layer is grown.
11. A third $\lambda/4$ polycrystalline silicon layer 21 is grown and doped electrically conducting at areas darkened in the diagram.
12. A third $\lambda/4$ silicon dioxide layer 25 is grown.
13. A third silicon dioxide layer 25 is patterned and etched.
14. A fourth $\lambda/4$ polycrystalline silicon layer 27 is grown onto the etched third silicon dioxide layer 25 and doped at areas darkened in the diagram.
15. A photoresist is applied and patterned free from the photoresist at the holes 14.
16. The holes 14 are made by plasma etching.
17. A resonator cavity 15 is made by etching-away material with, e.g., HF via holes 14.
18. Metallic bonding areas 16 are deposited using a mechanical mask.

Rear side:
1. A radiation absorbing layer 18 is grown.
2. A $\lambda/4$ silicon nitride layer 19 is grown.

We claim:

1. A single-channel infrared gas concentration measurement method comprising the following steps:
   generating a measuring signal by means of a radiant source;
   directing the measuring signal to a measurement object containing a gas mixture to be measured;
   bandpass filtering the measuring signal after being directed to the measurement object by implementing a single electrostatically tunable, short-resonator Fabry-Perot interferometer fabricated by surface micromachining techniques and having upper and lower resonator mirrors with a distance between said mirrors being equal to n µ/2 where n is from 1 to 3, said interferometer further having an aperture integrally provided in an interferometer structure and located adjacent to a side of said lower mirror which is opposite said upper mirror, said aperture being filled with silicon substrate, said bandpass filtering using at least two passband wavelengths; and
   detecting the measuring signal which has been filtered by means of a detector.

2. The method as defined in claim 1, wherein a concentration of carbon dioxide or carbon monoxide is measured.

3. The method as defined in claim 1, wherein the radiant source employed is an electrically modulatable radiant source.

4. The method as defined in claim 1, wherein such a Fabry-Perot interferometer is employed which is fabricated by surface micromachining techniques onto a silicon substrate so that one of said resonator mirrors is movable by means of a modulating electric field.

5. The method as defined in claim 1, wherein the measuring signal is subjected to filtering with a cut-off filter prior to detecting said measuring signal by the detector.

6. A single-channel infrared gas concentration measurement apparatus, comprising:
   a measuring
   a radiant source for generating a measuring signal;
   a measurement object containing a gas mixture to be measured and through which said measuring signal is sent;
   a variable bandpass filter for bandpass filtering of the measuring signal on at least two passband wavelengths, said bandpass filter being implemented by means of a single electrostatically tunable, short-resonator Fabry-Perot interferometer fabricated by surface micromachining techniques and having upper and lower resonator mirrors with a distance between said mirrors being equal to n λ/2 where n is from 1 to 3, said interferometer further having an aperture integrally provided in an interferometer structure and located adjacent to a side of said lower mirror which is opposite said upper mirror, said aperture being filled with silicon substrate; and
   a detector suited for detecting said filtered measuring signals.

7. The apparatus as defined in claim 6, wherein said radiant source is an electrically modulatable radiant source.

8. The apparatus as defined in claim 6, wherein said measurement apparatus incorporates a cut-off filter on a signal path prior to said detector.

9. An electrically tunable short-resonator Fabry-Perot interferometer fabricated by surface micromachining techniques for infrared gas concentration measurement, said interferometer comprising:
   upper and lower essentially parallel, adjacently aligned, semi-transmissive mirrors spaced at a distance (d) which is designed proportional to a center wavelength (λ) of the interferometer passband according to the formula:

$$d = n\lambda/2,$$

where n is an integer from 1 to 3 indicating an interferometer order number, said lower mirror having first and second opposite sides, said upper mirror being located closest to said first side of said lower mirror;
   control means for modulating the distance (d) between said resonator mirrors; and
   an aperture integrally provided in an interferometer structure and located closest to said second side of said lower mirror, said aperture being filled with silicon substrate.

10. The interferometer as defined in claim 9, wherein the structure around said aperture is fabricated from metal.

11. The interferometer as defined in claim 9, wherein the structure around said aperture is a polycrystalline membrane.

12. The interferometer as defined in claim 9, wherein said interferometer incorporates an integrated absorbing element to prevent transmission of radiation at undesirable wavelengths through said interferometer.

13. The interferometer as defined in claim 12, wherein a thickness of said absorbing element is λ/2.

14. The interferometer as defined in claim 9, wherein said interferometer incorporates holes at a rim of said upper mirror for etching away material from inside a resonator cavity.

* * * * *